(12) United States Patent
Almaskeen et al.

(10) Patent No.: US 10,871,431 B2
(45) Date of Patent: Dec. 22, 2020

(54) POROUS MICROMODEL NETWORK TO SIMULATE FORMATION FLOWS

(71) Applicant: Saudi Arabian Oil Company, Dhahran (SA)

(72) Inventors: Lyla Almaskeen, Saihat (SA); Amar Jaber M. Alshehri, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 72 days.

(21) Appl. No.: 16/386,897

(22) Filed: Apr. 17, 2019

(65) Prior Publication Data

US 2020/0333230 A1 Oct. 22, 2020

(51) Int. Cl.
| | | |
|---|---|---|
| *G01N 11/08* | (2006.01) | |
| *G01N 7/00* | (2006.01) | |
| *B09C 1/02* | (2006.01) | |
| *G01N 33/24* | (2006.01) | |

(52) U.S. Cl.
CPC ............... *G01N 11/08* (2013.01); *G01N 7/00* (2013.01); *G01N 33/241* (2013.01)

(58) Field of Classification Search
CPC ............. G01N 11/08; G01N 7/00; B09C 1/02
See application file for complete search history.

(56) References Cited

U.S. PATENT DOCUMENTS

| | | | |
|---|---|---|---|
| 4,882,763 A | | 11/1989 | Buchan et al. |
| 5,389,267 A | * | 2/1995 | Gorelick ............ B01D 17/0205 |
| | | | 210/170.07 |
| 7,300,227 B2 | * | 11/2007 | Li ............................ B09C 1/00 |
| | | | 210/747.7 |
| 9,895,730 B2 | * | 2/2018 | Hoag ........................ B09C 1/02 |

(Continued)

FOREIGN PATENT DOCUMENTS

CN 105869496 8/2016

OTHER PUBLICATIONS

PCT International Search Report and Written Opinion issued in International Application No. PCT/US2020/028104 dated Jul. 24, 2020, 15 pages.

(Continued)

*Primary Examiner* — Jewel V Dowtin
(74) *Attorney, Agent, or Firm* — Fish & Richardson P.C.

(57) ABSTRACT

A porous micromodel network to simulate formation flows includes a substrate, two or more porous micromodels formed on the substrate and a fluid inlet formed on the substrate. The first porous micromodel defines a first fluidic flow pathway and is representative of a first hydrocarbon-carrying formation. Flow through the first fluidic flow pathway is representative of flow through the first hydrocarbon-carrying formation. The second porous micromodel is fluidically isolated from the first porous micromodel. The second porous micromodel defines a second fluidic flow pathway different from the first fluidic flow pathway. The second porous micromodel is representative of a second hydrocarbon-carrying formation different from the first hydrocarbon-carrying formation. Flow through the second fluidic flow pathway is representative of flow through the second hydrocarbon-carrying formation. The fluid inlet is fluidically configured to simultaneously flow fluid to the first fluidic flow pathway and the second fluidic flow pathway.

22 Claims, 5 Drawing Sheets

(56) References Cited

U.S. PATENT DOCUMENTS

| | | | |
|---|---|---|---|
| 10,024,777 B2* | 7/2018 | Molla | G01N 35/1095 |
| 2005/0279713 A1* | 12/2005 | Osborn | C02F 1/78 |
| | | | 210/760 |
| 2016/0123890 A1 | 5/2016 | He et al. | |
| 2016/0153954 A1 | 6/2016 | Shor et al. | |
| 2016/0305237 A1* | 10/2016 | Klemin | E21B 25/00 |
| 2020/0215539 A1* | 7/2020 | Levant | B81C 99/0085 |

OTHER PUBLICATIONS

Al-Dousary, "Determining Pore Level Mechanisms of Alkaline Surfactant Polymer Flooding using a Micromodel," SPE 165572-STU, SPE International Student Paper Contest at the SPE Annual Technical Conference and Exhibition, Oct. 8-10, 2012, Society of Petroleum Engineers, Jan. 1, 2012, 16 pages.

Al-Otaibi et al., "Enhancing Oil Recovery by CO2 Emulsions: Better Sweep Efficiency and Improved Recovery," Saudi Aramco Journal of Technology, Fall 2017, 9 pages.

Al-Shehri et al., "Pore-Level Mechanics of Forced and Spontaneous Imbibition of Aqueous Surfactant Solutions in Fractured Porous Media," SPE 124946, presented at the 2009 SPE Annual Technical Conferene and Exhibition, Oct. 4-7, 2009, Society of Petroleum Engineers, Jan. 1, 2009, 17 pages.

Buchgraber et al., "A Microvisual Study of the Displacement of Viscous Oil by Polymer Solutions," SPE 122400, Society of Petroleum Engineers, Jun. 1, 2011, 12 pages.

Koivu, "Analysis of fluid flow throught porous media based on X-ray micro-tomographic reconstructions," thesis for degree of Doctor of Philosphy from University of Jyvaskyla, Oct. 2, 2010, 90 pages.

Song et al., "Chip-off-the-old-rock: the study of reservoir-relevant geological processes with real-rock micromodels," Lab-on-a-Chip Publication, Nov. 2014, 9 pages.

* cited by examiner

POROUS MICROMODEL NETWORK TO SIMULATE FORMATION FLOWS

TECHNICAL FIELD

This disclosure relates to evaluating fluid flow through hydrocarbon-carrying formations.

BACKGROUND

Hydrocarbons (for example, oil, natural gas, or combinations of them) entrapped in formations can be raised to the surface, that is, produced, using wells formed through the formations. Usually, the hydrocarbons are entrapped in the formations under pressure sufficient to flow the hydrocarbons through pores of the formations into the wells. Formations can be of different types, for example, carbonate or sandstone, and can have different porosities that affect the flow of the hydrocarbons through the formations.

SUMMARY

This specification describes technologies relating to a porous micromodel network to simulate formation flows. Information about the flow of hydrocarbons or other fluids (for example, water, brine, or chemicals) through a formation can allow efficiently managing the recovery of hydrocarbons entrapped in the formations.

Certain aspects of the subject matter described here can be implemented as an apparatus that includes a substrate, two porous micromodels formed on the substrate and a fluid inlet formed on the substrate. The first porous micromodel defines a first fluidic flow pathway and is representative of a first hydrocarbon-carrying formation. Flow through the first fluidic flow pathway is representative of flow through the first hydrocarbon-carrying formation. The second porous micromodel is fluidically isolated from the first porous micromodel. The second porous micromodel defines a second fluidic flow pathway different from the first fluidic flow pathway. The second porous micromodel is representative of a second hydrocarbon-carrying formation different from the first hydrocarbon-carrying formation. Flow through the second fluidic flow pathway is representative of flow through the second hydrocarbon-carrying formation. The fluid inlet is fluidically configured to simultaneously flow fluid to the first fluidic flow pathway and the second fluidic flow pathway.

An aspect combinable with any of the other aspects can include the following features. The first hydrocarbon-carrying formation is an ideal hydrocarbon-carrying formation. The first porous micromodel includes first porous media defining multiple first pores that define the first fluidic flow pathway. The multiple first pores have substantially identical dimensions.

An aspect combinable with any of the other aspects can include the following features. The multiple first pores are substantially equidistantly spaced apart from each other.

An aspect combinable with any of the other aspects can include the following features. Each of the multiple first pores is circular. The multiple first pores have substantially the same diameter.

An aspect combinable with any of the other aspects can include the following features. The second hydrocarbon-carrying formation is an actual hydrocarbon-carrying formation. The second porous micromodel includes second porous media defining multiple second pores that define the second fluidic flow pathway. The multiple second pores have a range of varying dimensions.

An aspect combinable with any of the other aspects can include the following features. The multiple second pores are spaced at varying distances from each other.

An aspect combinable with any of the other aspects can include the following features. The apparatus includes a first porous micromodel inlet formed on the substrate at an edge of the first porous micromodel. The first porous micromodel inlet is fluidically connected to the fluid inlet formed on the substrate. The first porous micromodel fluid inlet is configured to receive fluid from the fluid inlet and to flow the fluid into the first fluidic pathway. The apparatus includes a second porous micromodel fluid inlet formed on the substrate at an edge of the second porous micromodel. The second porous micromodel fluid inlet is fluidically connected to the fluid inlet formed on the substrate. The second porous micromodel fluid inlet is configured to receive fluid from the fluid inlet and to flow the fluid into the second fluidic pathway.

An aspect combinable with any of the other aspects can include the following features. The first porous micromodel fluid inlet and the second porous micromodel fluid inlet have the same dimensions.

An aspect combinable with any of the other aspects can include the following features. The apparatus includes a first porous micromodel fluid outlet formed on the substrate at another edge of the first porous micromodel. The first porous micromodel fluid outlet is configured to permit the fluid flowed through the first fluidic pathway to exit the first porous micromodel. The apparatus includes a second porous micromodel fluid outlet formed on the substrate at another edge of the second porous micromodel. The second porous micromodel fluid outlet is configured to permit the fluid flowed through the second fluidic pathway to exit the second porous micromodel.

An aspect combinable with any of the other aspects can include the following features. The substrate is made of silicon wafer. The apparatus includes a transparent plate that fluidically seals the first porous micromodel and the second porous micromodel.

An aspect combinable with any of the other aspects can include the following features. The apparatus includes a wall between the first porous micromodel and the second porous micromodel. The wall fluidically isolates the first porous micromodel from the second porous micromodel.

Certain aspects of the subject matter described here can be implemented as a laboratory-scale system. The system includes a porous micromodel network including multiple porous micromodels that are different from each other and that are fluidically isolated from each other. Each porous micromodel defines a respective fluidic flow pathway. Each porous micromodel is representative of a respective hydrocarbon-carrying formation. Flow through each fluidic flow pathway is representative of flow through the respective hydrocarbon-carrying formation. The system includes a flow device configured to simultaneously flow fluid through the porous micromodel network.

An aspect combinable with any of the other aspects can include the following features. The system includes a flow manifold including an inlet fluidically coupled to the flow device and multiple outlets, one outlet per porous micromodel. The multiple outlets are fluidically coupled to multiple porous micromodel inlets. The flow manifold is configured to receive fluid from the fluid flow device and simultaneously flow the fluid to the porous micromodel network.

An aspect combinable with any of the other aspects can include the following features. The system includes multiple pressure gauges, one pressure gauge per porous micromodel. The multiple pressure gauges are coupled to the respective multiple porous micromodels. Each pressure gauge is configured to measure a flow pressure of the fluid through the respective porous micromodel.

An aspect combinable with any of the other aspects can include the following features. The system includes a flow visualization device spatially positioned relative to the porous micromodel network. The flow visualization device is configured to capture flow of the fluid through each porous micromodel as well as the fluid saturation after each stage of the experiment.

An aspect combinable with any of the other aspects can include the following features. The flow visualization device includes a camera.

An aspect combinable with any of the other aspects can include the following features. The flow visualization device includes a microscope coupled to the camera.

An aspect combinable with any of the other aspects can include the following features. The fluid flow device includes a pump configured to pump the fluid through the porous micromodel network.

An aspect combinable with any of the other aspects can include the following features. The system includes multiple fluid containers. Each fluid container carries a hydrocarbon-carrying formation fluid, or water or chemical. The pump is configured to draw the hydrocarbon-carrying formation fluid from one of the multiple fluid containers and flow the fluid simultaneously through the porous micromodel network.

Certain aspects of the subject matter described here can be implemented as a method. A fluid is flowed simultaneously through multiple laboratory-scale porous micromodels of a porous micromodel network. The multiple porous micromodels are different and fluidically isolated from each other. Each porous micromodel defines a respective fluidic flow pathway. Each porous micromodel is representative of a respective hydrocarbon-carrying formation. Flow through each fluidic flow pathway is representative of flow through the respective hydrocarbon-carrying formation. The flow of the fluid through the multiple porous micromodels is imaged and flow through each respective hydrocarbon-carrying formation is evaluated based on imaging the flow of the fluid as well as imaging the fluid saturation at the end of each stage of the experiment.

An aspect combinable with any of the other aspects can include the following features. The multiple laboratory-scale micromodels includes two porous micromodels and the multiple fluids includes two same fluids.

An aspect combinable with any of the other aspects can include the following features. The multiple laboratory-scale micromodels are different from each other.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This disclosure describes a laboratory-scale apparatus to study flow through hydrocarbon-carrying formations. As described later, the apparatus includes multiple scaled-down models of a hydrocarbon-carrying formation. Each model is large enough to effectively mimic flow of fluids through an actual hydrocarbon-carrying formation that the model represents. Yet, the model is small enough to fit on a laboratory bench top and be connected to fluidic components such as pumps, pressure gauges, tubes, and valves, and the like. A model is referred to as a micromodel in this disclosure to communicate that the pores in the model are measured in micrometers, which is a measurement scale used to measure pores and grains of an actual hydrocarbon-carrying formation. In some implementations, a micromodel can be about 4 centimeters (cm) long and about 1.5 cm wide.

This disclosure describes studying flow through porous micromodels that represent hydrocarbon-carrying formations. In some implementations, multiple porous media micromodels are fabricated on a common substrate. Each micromodel is a porous media that represents a different type of hydrocarbon-carrying formation, for example, a carbonate formation, a sandstone formation or similar hydrocarbon-carrying formation.

In some implementations, one of the micromodels can be an ideal micromodel, which is described later. Each micromodel is fluidically isolated from each other such that fluid can flow through a micromodel, but not between micromodels. Each micromodel has an inlet and an outlet for fluid flow. The inlets of all the micromodels are fluidically connected to a common inlet. Fluid from a fluid driving source (for example, a pump) is flowed simultaneously to the inlets of all the micromodels. The respective porosity of each micromodel dictates the nature of flow of the fluid through that micromodel. By visualizing the flow of the fluid through and measuring the differential fluid pressure across each micromodel, the fluid flow properties of each micromodel can be studied. Such fluid flow properties are representative of the scaled-up hydrocarbon-carrying formations that the respective micromodels represent. For example, the fluid flow properties can be used to evaluate enhanced oil recovery (EOR) through the hydrocarbon-carrying formations, evaluate EOR chemical flow through the hydrocarbon-carrying formations and perform conformance control studies. For example, different gels can be flowed through the multiple micromodels and the gelation time of the different gels studied to evaluate an effect of flowing the gels through the actual hydrocarbon-carrying formations.

Implementations of the subject matter disclosed here allows capturing heterogeneities of different hydrocarbon-carrying formations on a common substrate. Simultaneously performing flow studies through multiple micro-models reduces study time and resources.

Figure 1A:
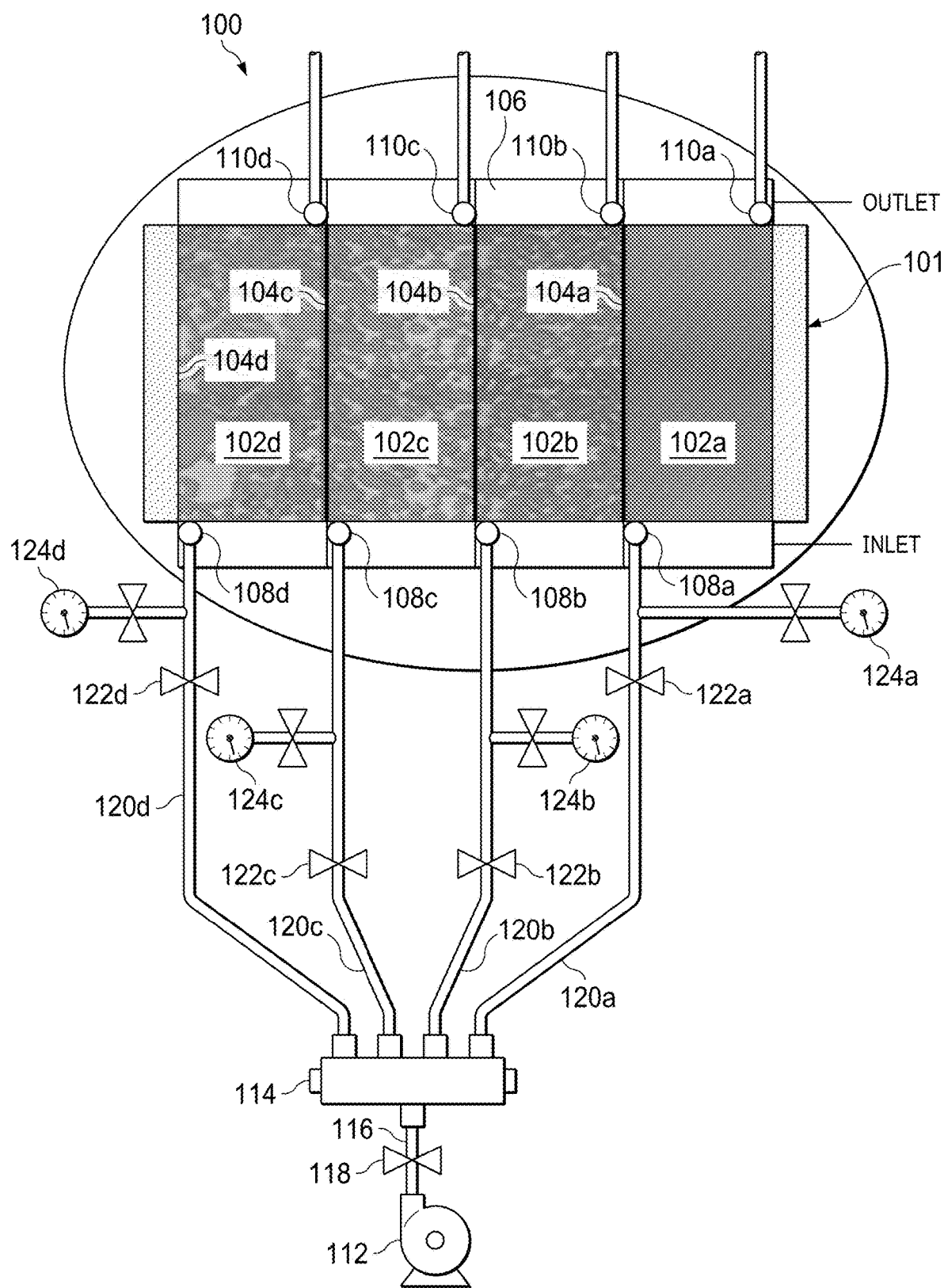
FIG. 1A is a schematic diagram of a micromodel system for simulating flow through hydrocarbon-carrying formations.

FIG. 1A is a schematic diagram of a micromodel system 100 for simulating flow through hydrocarbon-carrying formations. The micromodel system 100 is a laboratory-scale system, that is, a system designed and constructed to be placed on a laboratory bench-top and operated using laboratory equipment operable either manually or automatically, for example, using a computer system. The system 100 includes a porous micromodel network 101 that includes multiple porous micromodels. In the example implementation shown in FIG. 1A, the system 100 includes four porous media—a first micromodel 102a, a second micromodel 102b, a slice of actual sandstone 102c, a fourth micromodel 102d. At minimum, the system 100 includes two micromodels, but, in some implementations, can include three or more than four micromodels. Each porous micromodel is a porous media through which fluid can flow. The porosity of each micromodel is fabricated to represent a respective hydrocarbon-carrying formation. In some implementations, each porous micromodel is fabricated by etching to a pre-determined depth that can range between 20 micrometers ($\mu$m) and 40 $\mu$m. The etching depth is determined to maintain adequate permeability of the pore network to fluid flow.

Figure 3A:
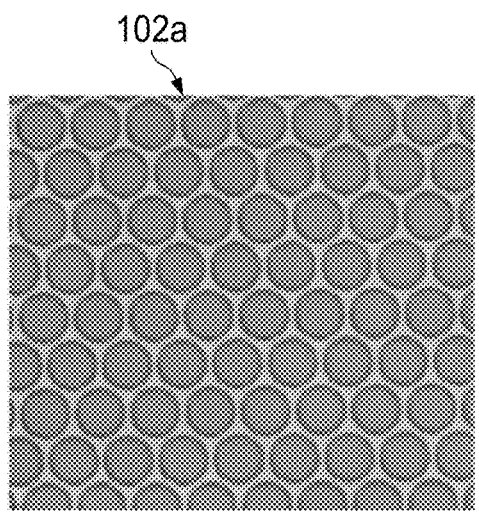
FIG. 3A is a schematic diagram of a pore network of an ideal micromodel.

For example, the first micromodel 102a can be an ideal micromodel. FIG. 3A is a schematic diagram of the ideal micromodel. The ideal micromodel is a homogeneous porous medium in which the geometry of the pores and throats (that is, the spacing between pores) have substantially identical dimensions throughout the network. The pores of the first micromodel 102a are substantially circular and the dimensions of each pores are substantially identical. In this context, the term "substantially" encompasses variations that are artifacts of the fabrication technique. For example, "substantially circular" pore means that the pore is fabricated to be perfectly circular but the final pore may not be perfectly circular due to fabrication artifacts. In another example, "substantially identical" dimensions means that the dimensions are fabricated to be identical but the dimensions may not be perfectly identical due to fabrication artifacts.

Figure 3B:
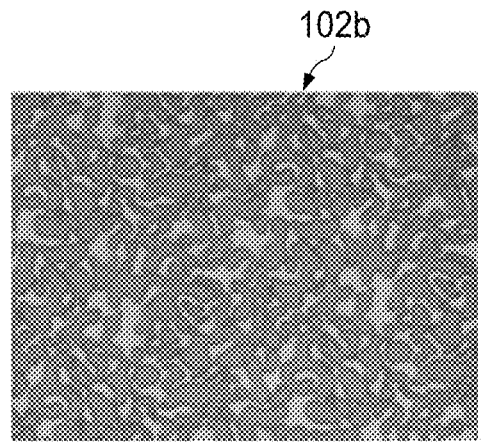
FIG. 3B is a schematic diagram of a pore network of a micromodel simulating a sandstone formation.

In the example system 100 shown in FIG. 1A, the second micromodel 102b represents a simulated sandstone formation. Sandstone formations are generally homogeneous having pores of sizes that fall within a narrow range of sizes and that are spaced apart at a range of differing distances. FIG. 3B is a schematic diagram of a pore network of a micromodel simulating a sandstone formation. Unlike the ideal first micromodel 102a with the substantially identical pores and pore sizes, the pores of the second micromodel 102b differ in appearance and have a range of pore sizes that mimic those of the sandstone formation that the second micromodel 102b represents. For example, the pore sizes can range between 50 $\mu$m to 300 $\mu$m, and fall within sub-ranges within this range based on the pore size of the actual formation that the micromodel simulates.

Figure 3C:
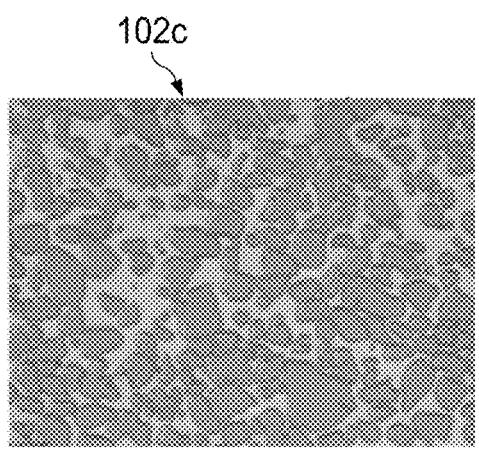
FIG. 3C is a schematic diagram of a pore network of an actual sandstone formation.

In the example system 100 shown in FIG. 1A, the slice of actual sandstone 102c represents an actual sandstone formation. FIG. 3C is a schematic diagram of a pore network of an actual sandstone formation. The actual sandstone schematically shown in FIG. 3C is more permeable than the simulated sandstone schematically shown in FIG. 3B. Also, the range of pore sizes of the micromodel 102b is smaller than the range of pore sizes of the actual sandstone schematically shown in FIG. 3C.

Figure 3D:
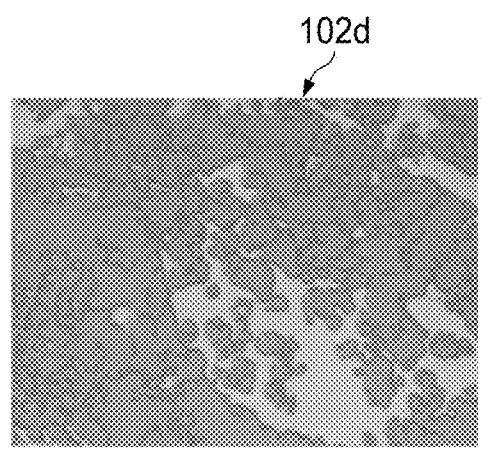
FIG. 3D is a schematic diagram of a pore network of a micromodel simulating a carbonate formation.

In the example system 100 shown in FIG. 1A, the fourth micromodel 102d represents a carbonate formation. FIG. 3D is a schematic diagram of a pore network of a carbonate formation. Compared to sandstone formations, carbonate formations are more heterogeneous and have a broader range of pore sizes. Certain portions of carbonate formations are tighter, that is, have smaller pore sizes, than other portions. The fourth micromodel 102d is fabricated to reflect the characteristics of the carbonate formation.

The porous structure of each micromodel defines a fluidic flow pathway through which fluid can be flowed, for example, under pressure. Because each micromodel is designed and constructed to represent a respective formation, fluid flow through the fluidic pathway in each micromodel represents fluid flow through the actual formation itself.

In some implementations, each micromodel is formed to have a regular, geometric shape, for example, rectangular or square. Two parallel edges of the shape can define two walls that separates the micromodel from two adjacent micromodels on either side or can define a separating wall and an edge of the system 100 itself. The two remaining parallel edges of the shape can represent fractures in the formation.

In some implementations, fluid inlets are formed on the substrate to permit fluid flow into each micromodel. For example, a first fluid inlet 108a, a second fluid inlet 108b, a third fluid inlet 108c and a fourth fluid inlet 108d can be formed adjacent to an edge of the first micromodel 102a, the second micromodel 102b, the slice of actual sandstone 102c and the fourth micromodel 102d, respectively. To maintain substantially constant fluid flow conditions across all the micromodels in the system 100, the dimensions of the fluid inlets and the relative position of the fluid inlets adjacent the relative edges of the micromodels can be the same for all the micromodels. Similarly, a first fluid outlet 110a, a second fluid outlet 110b, a third fluid outlet 110c and a fourth fluid outlet 110d can be formed adjacent to the edge of the first micromodel 102a, the second micromodel 102b, the slice of actual sandstone 102c and the fourth micromodel 102d, respectively, that is opposite and parallel to the edge adjacent to which the inlets are formed. To maintain substantially constant fluid flow conditions across all the micromodels in the system 100, the dimensions of the fluid outlets and the relative position of the fluid outlets adjacent the relative edges of the micromodels can be the same for all the micromodels. In some implementations, the inlets and outlets can be openings, punctures or orifices that allow the fluid to enter and exit the network connected to tubings, for example, tubings of 1/8" diameter, through fittings, for example, 1/8" inch fittings.

Figure 1B:
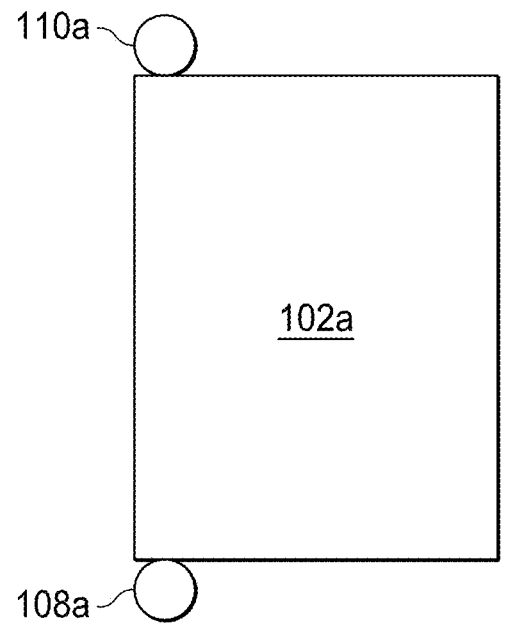
FIGS. 1B and 1C are each schematics of a micromodel with a respective inlet and an outlet.
Figure 1C:
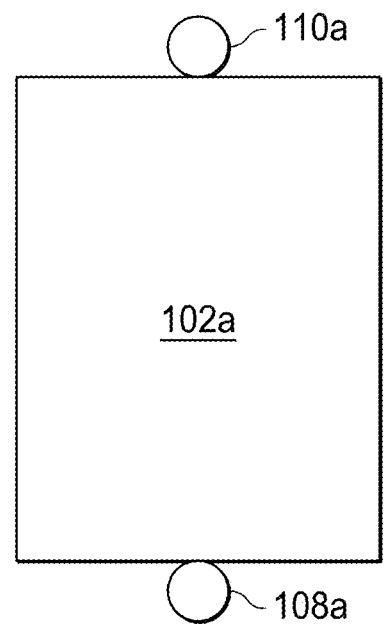

In the schematic of FIG. 1A, the fluid inlet 108a and the fluid inlet 108b are shown as formed adjacent to diametrically opposite edges of the micromodel. In some implementations, the fluid inlet can be formed at different locations relative to the edges of the micromodel. FIG. 1B shows a schematic of the micromodel 102a in which the fluid inlet 108a and the fluid outlet 110a are formed adjacent the same longitudinal edge of the micromodel 102a. FIG. 1C shows a schematic of the micromodel 102a in which the fluid inlet 108a and the fluid outlet 110a are formed adjacent a center of each of parallel edges of the micromodel 102a. The fluid inlet and the fluid outlet of each micromodel in the porous micromodel network 101 can be in the same respective locations. By varying the locations of the fluid inlets and the fluid outlets, different fluid flow conditions at the inlet and the outlet can be tested for each porous micromodel. Also, by forming the inlets and the outlets at the same locations for the multiple micromodels in the same network, the same fluid flow conditions can be created simultaneously to all the micromodels in the network. In some implementations, the fluid inlet and the fluid outlet can be formed adjacent the vertical edges of the micromodel instead of adjacent the horizontal edges as shown in the schematics. In some implementations, the fluid inlet and the fluid outlet can be formed adjacent each other along the same edge. In some implementations, the fluid inlet and the fluid outlet can be formed adjacent to respective perpendicular edges of the micromodel. The location of the fluid inlet and the fluid outlet can be selected based on injection patterns, that is, real-world locations through which fluids will be injected into and flowed out of formations that are represented by the micromodels. By doing so, real world injection patterns can be simulated.

The multiple micromodels are formed on a common substrate 106. For example, the substrate 106 is a silicon wafer on which the multiple micromodels are etched. Alternatively, glass, polydimethoxysilane (PDMS) substrate or any other etchable substrate can be used.

In general, the substrate 106 can be made from any material that can be etched or otherwise fabricated to form the porous micromodels. In some implementations, the inlets and outlets can be formed on the substrate 106, for example, by etching during fabrication of the system 100. In some implementations, the inlets and the outlets can be formed as openings in the substrate 106, for example, by drilling, to which fluidic fittings can be attached to flow fluid into and out of the micromodels.

The micromodels can be fluidically isolated from each other. For example, a first wall 104a, a second wall 104b and a third wall 104c can be formed between the micromodels 102a and 102b, the micromodels 102b and 102c and the micromodels 102c and 102d, respectively. For example, the portion of the substrate 106 that forms each wall may not be etched during fabrication. Consequently, when the system 100 is fabricated, fluid cannot flow past or through a wall from one micromodel to an adjacent micromodel that is fluidically isolated by the wall. Thus, in a side view, each micromodel and the wall appear as pillars attached to the substrate 106 at the bottom and open at the top.

The system 100 includes a transparent plate, for example, a glass plate or plate made of other transparent material, that is positioned above and fluidically seals the multiple micromodels in the system 100. For example, after microfabrication of the multiple micromodels, the inlets, the outlets and any other features needed to operate the system 100 as described in this disclosure, the transparent plate is positioned on top of the substrate 106 and sealed, for example, bonded, to the top of each micromodel and the walls.

In some implementations, the system 100 can be fluidically coupled to a fluid flow device 112, for example, a pump. The fluid flow device 112 can simultaneously flow fluid through the multiple micromodels in the system 100. For example, the fluid flow device 112 can be connected to a fluid manifold 114 that includes one inlet and as many outlets as the system 100 includes micromodels. In some implementations, the fluid flow device 112 can be connected to the fluid manifold 114 using a tube 116 and, in some instances, by a valve 118 to control fluid flow from the fluid flow device 112 to the fluid manifold 114.

For the example system 100, four tubes 120a, 120b, 120c and 120d can connect outlets of the fluid manifold 114 (identified by the label "OUTLET" in FIG. 1A) to the four inlets 108a, 108b, 108c and 108b, respectively, (identified by the label "INLET" in FIG. 1A). Flow through the four tubes can be controlled using four respective valves 122a, 122b, 122c and 122d. Four pressure gauges 124a, 124b, 124c, 124d can be fluidically coupled to the four tubes 120a, 120b, 120c, and 120d, respectively. Each pressure gauge (or other differential pressure sensor) can sense and measure the pressure drop across the corresponding micromodel.

Figure 2:
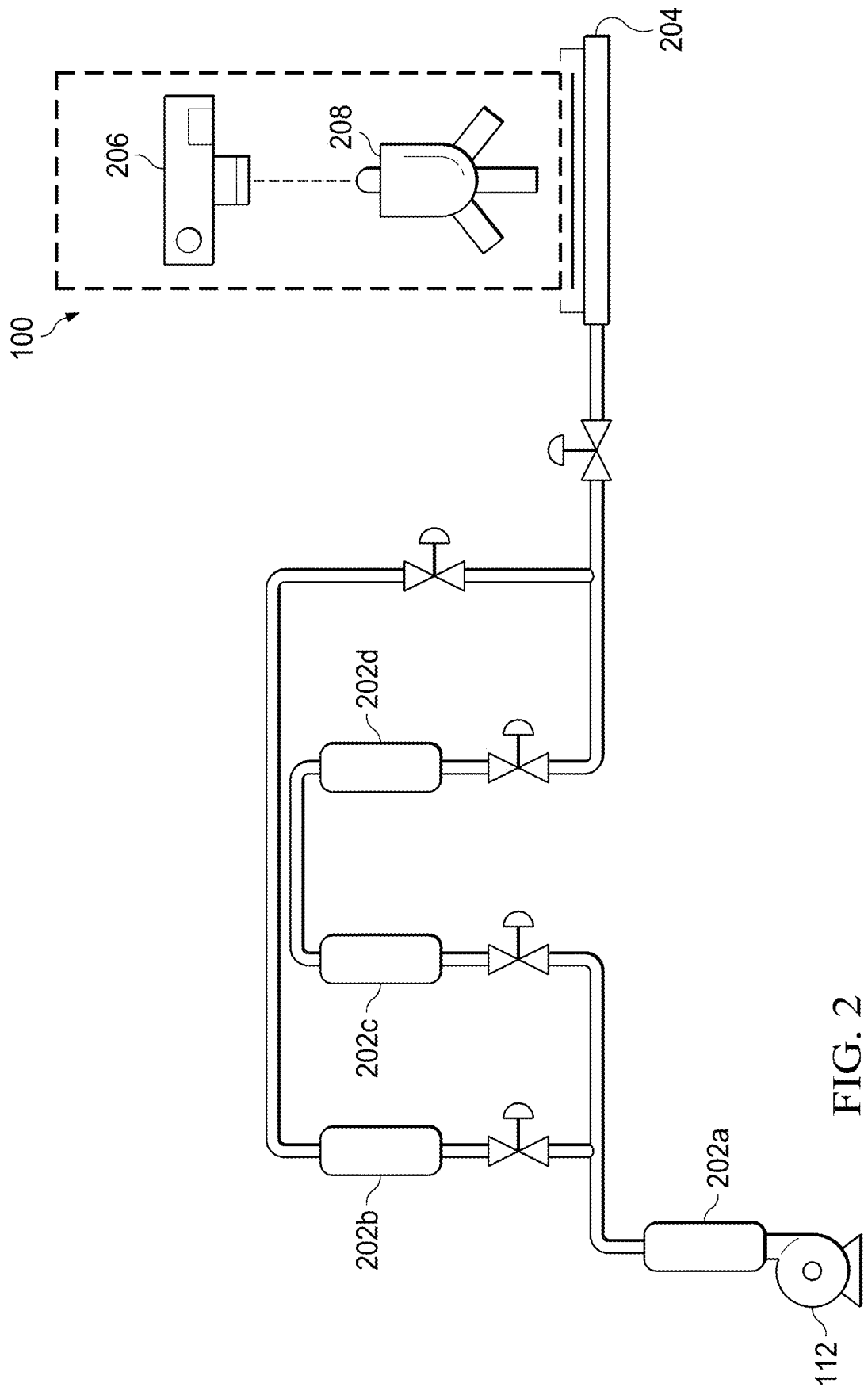
FIG. 2 is another schematic diagram of the micromodel system of FIG. 1A.

FIG. 2 is another schematic diagram of the micromodel system 100. In some implementations, the system 100 is fluidically coupled to multiple fluid containers, for example, fluid containers 202a, 202b, 202c, 202d, each of which is fluidically coupled to the fluid flow device 112 through tubes and valves. For example, the fluid flow device 112 can draw a pre-determined volume of fluid from one of the containers and simultaneously flow the drawn fluid through all the micromodels in the system 100. The fluids in the containers can include naturally-occurring formation fluids such as crude oil or natural gas or other fluids injected into the formation such as chemicals including surfactants or polymers. One of the containers can include water, specifically de-ionized water, that can be flowed through the micromodels after each flow study to purge the micromodels in preparation for a subsequent flow study. In some implementations, additional containers carrying fluids such as filtered crude oil, filtered brine, polymers, surfactants, foams, gels, organic chemicals used as crude oil substitutes, alcohols (for example, methanol, ethanol), toluene, gases (for example, $CO_2$) can be coupled to the micromodels.

In some implementations, the micromodel system 100 can be positioned on a micromodel holder 204 that includes the fluid inlet from which the fluid is simultaneously flowed into the multiple micromodels and a fluid outlet to collect the fluid flowing out of the multiple micromodels. A flow visualization device can be spatially positioned relative to the system 100. For example, the flow visualization device can include a camera 206 that can capture images (such as static images or video or both) of the flow of the fluid through each micromodel. The flow visualization device can also include a microscope 208 that can be coupled to the camera 206 to provide zoomed-in images or video of the flow for capture by the camera 206. All fluidic seals can be implemented using seals such as O-rings. The micromodel system 100 and other components shown in FIGS. 1A-1C and 2 can be positioned and operated on a laboratory bench-top.

In some implementations, the micromodel system can be fabricated as described in the following paragraphs. A silicon wafer of pre-determined dimensions is selected. A mask is selected for each micromodel. The mask is analogous to a photographic negative. The mask carries an image of the porous network to be etched on the silicon wafer to form the micromodel. For example, a first mask carries an image of the ideal first formation 102a, a second mask carries an image of the second, actual sandstone formation 102b, a third mask carries an image of the third, simulated sandstone formation 102c, and a fourth mask carries an image of the carbonate formation 102d. The images carried by the multiple masks are then etched on the silicon wafer in a nanofabrication facility with a clean room.

In a first step, the silicon wafer is dehydrated in a dehydrating oven for a duration, for example, about 30 minutes. Dehydration is performed at a temperature, for example, 150 degrees Centigrade (° C.) and involves priming the water with hexamethyldisilazane (HMDS) to improve the photoresist adhesion to the wafer. In a second step, the silicon wafer is then coated with a layer of photoresist, for example, 1.0-1.6 micrometers (µm). In a third step, the multiple masks are positioned adjacent to each other on the silicon wafer. A soft contact program with an exposure of about 2.6 seconds and a gap width of about 40 µm is selected to expose the photoresist to light through the masks. The exposure transfers the pore network of each micromodel from the mask onto the photoresist. In a fourth step, the pore network is developed to remove the excess photoresist. In a fifth step, the developed wafers are etched, for example, in an inductive charged plasma etcher. The input etching time is selected based on the desired etching depth. After etching the wafer, in a sixth step, ports are drilled at the corners of each network. The wafer is then cleaned and bonded with a glass wafer in a bath of sulfuric acid and hydrogen peroxide, for example, in a 9:1 ratio. In a seventh step, the wafer is anodically bonded with the glass wafer under a voltage, for example, of about 1200 volts. In an eighth step, the etched silicon wafer is heated for a duration, for example, 45 minutes, to a temperature, for example, 350° C. In a ninth step, the wafer is then dusted to remove any particle residue. In a tenth step, a clean glass wafer is placed on top of the silicon wafer for a duration, for example, two minutes. In an eleventh step, the glass wafer is electrically bonded to the silicon wafer to form the micromodel system 100.

Figure 4:
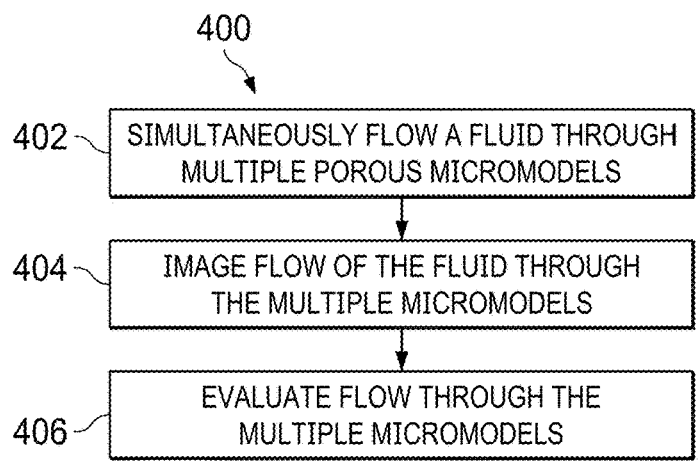
FIG. 4 is a flowchart of an example of a process for evaluating flow through hydrocarbon-carrying formations using the micromodel system of FIG. 1A.

FIG. 4 is a flowchart of an example of a process 400 for evaluating flow through hydrocarbon-carrying formations using the micromodel system of FIG. 1A. The process 400 can be performed by a laboratory technician. Alternatively or in addition, some or all aspects of the process 400 can be automatically performed, for example, using a computer system. At 402, a fluid is simultaneously flowed through multiple porous micromodels, for example, the multiple micromodels of the micromodel system 100. At 404, flow and saturation of the fluid through the multiple micromodels is imaged. At 406, flow through the multiple micromodels is evaluated.

Evaluating the flow through the multiple micromodels includes determining an initial flow rate for each micromodel using Eq. 1.

$$\overline{Q}_{ni}\left(\frac{cc}{s}\right) = \frac{K(D) \cdot A(\text{cm}^2) \cdot \Delta P(\text{atm})}{\mu(cp) \cdot L(\text{cm})} \qquad \text{Eq. 1}$$

In Eq. 1, $\overline{Q}_{ni}$, measured in cubic centimeters per second (cc/s) is the flow rate through a micromodel. In Eq. 1, A is the cross-sectional area of a porous micromodel. All the micromodels in the system 100 have the same cross-sectional area which is equal to the etching depth (for example, substantially 30 microns) multiplied by the width (for example, substantially 1 centimeter (cm)). In this disclosure, "substantially" encompasses a deviation between plus or minus 5% to 10% of the mentioned numerical value. In Eq. 1, L is the length of the micromodel. All the micromodels in the system 100 have the same length of substantially 4 cm to 5 cm. In Eq. 1, µ is the viscosity of the fluid flowed through the micromodel and can vary depending on the fluid flowed, for example, water, crude oil, other chemicals such as surfactants. Permeability of a micromodel is measured using water which has a viscosity of substantially 1.0 centiPoise (cP). In Eq. 1, K(D) is the permeability of each micromodel which will vary. One technique to measure permeability is to flow a fluid having known properties (for example, water) through one micromodel at a time, measuring pressure across the micromodel and calculating permeability. In Eq. 1, ΔP is a pressure drop across the micromodel measured using the respective pressure gauge.

The total flow rate through the system 100 is then the sum of the flow rates through each micromodels. This is the minimum flow rate at which the fluid flow device 112 is operated to ensure that all the micromodels receive sufficient fluid. The total flow rate is selected such that the pressure drop across each micromodel does not exceed a pressure threshold, for example, 50 pounds per square inch (psi), preferably remains between 20 psi and 30 psi.

Figure 5:
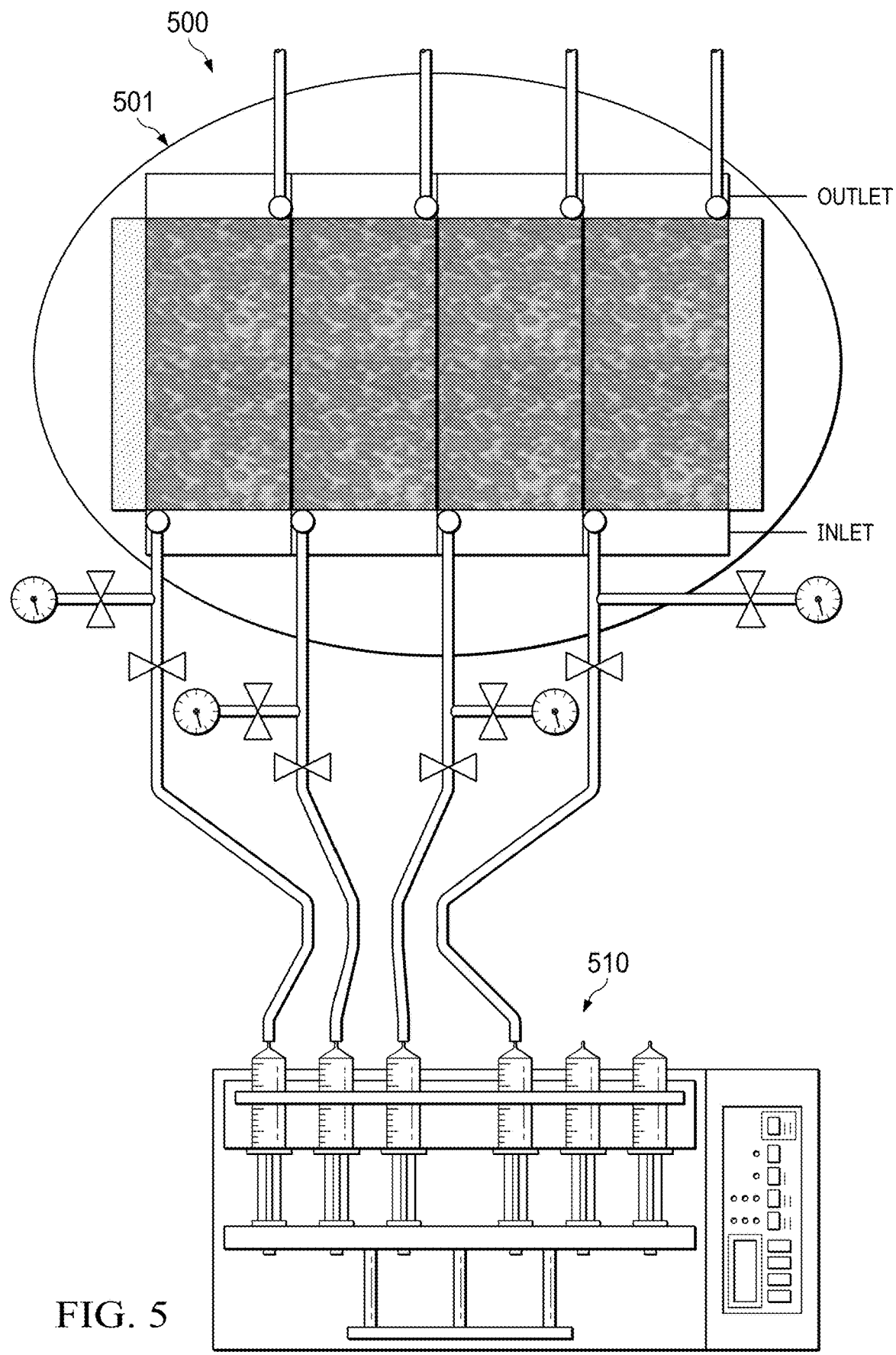
FIG. 5 is a schematic diagram of a micromodel system for simulating flow of different fluids.

FIG. 5 is a schematic diagram of a micromodel system 500 for simulating flow of different fluids. The fluids flowed through the micromodel system 500 can be the same depending on the objective of the study. The micromodel system 500 includes a porous micromodel network 501 that is substantially similar to the porous micromodel network 101 (FIG. 1). That is, the network 501 includes multiple porous micromodels positioned adjacent each other, each having a respective fluid inlet and a respective fluid outlet. The network 501 differs from the network 101 in that all the micromodels in the network 501 are identical to each other. That is, all the micromodels in the network 501 are the first micromodel 102a or the second micromodel 102b or the slice of actual sandstone 102c or the fourth micromodel 102d. With this arrangement, different types of fluids can be flowed through multiple, identical micromodels under identical fluid flow conditions, for example, pressure, differential pressure, viscosity, flow rate or similar fluid flow conditions. Doing so allows simultaneously evaluating the flow patterns of different models through the same micromodel. In some applications of the micromodel system 500, the viscosity of the flowing fluids can be the same or different. In some applications, the flow rate can be different. For example, the same fluid can be flowed at different flow rates.

In some implementations, a syringe pump 510 can be used to flow fluid under identical flow conditions through the network 501. For example, the syringe pump 501 can be capable of driving multiple syringes simultaneously. The number of syringes is equal to the number of micromodels in the network 501. Each of the multiple syringes can be fluidically coupled to a respective fluidic inlet of one of the micromodels in the network 501. Each of the multiple syringes can carry a different fluid to be flowed through the respective micromodel. In an example implementation in which the network 501 includes three micromodels, a first syringe pump can carry de-ionized water, a second syringe can carry crude oil and a third syringe can carry a drilling fluid. The three syringes can have the same dimensions. The syringe pump 510 can apply an equal pressure to the three syringes causing the three different fluids to be flowed through identical micromodels in the network 501 under identical flow conditions. However, because the fluids themselves are different, the flow pattern of each fluid through the respective micromodel will be different. The flow pattern can be evaluated by imaging the fluid flow or based on saturation of the fluid in each micromodel. In some implementations, instead of a single syringe pump 510 that drives multiple syringes, multiple syringe pumps, each capable of driving only one syringe, can be fluidically coupled to respective micromodels to flow different fluids through identical micromodels under identical flow conditions. In some applications of the network 501, the different syringes can carry the same fluid but apply different flow rates to test different properties of the fluids. In some applications of the network 501, the pressures exerted by the different pumps can be different depending on the properties of different fluids flowed by the different pumps.

In sum, the network 101 can be implemented to simultaneously flow the same fluid under the same fluid flow conditions through different micromodels. By doing so, heterogeneity of micromodels in the network 101 and conformance control studies can be performed. In some implementations, the network 501 can be implemented to simultaneously flow different fluids under the same fluid flow conditions through the same micromodels. By doing so, flow parameters of different fluid or chemical formulations can be studied.

Thus, particular implementations of the subject matter have been described. Other implementations are within the scope of the following claims.

The invention claimed is:

1. An apparatus comprising:
a substrate;
a first porous micromodel formed on the substrate, the first porous micromodel defining a first fluidic flow pathway, the first porous micromodel representative of a first hydrocarbon-carrying formation, flow through the first fluidic flow pathway representative of flow through the first hydrocarbon-carrying formation;
a second porous micromodel formed on the substrate, the second porous micromodel fluidically isolated from the first porous micromodel, the second porous micromodel defining a second fluidic flow pathway different from the first fluidic flow pathway, the second porous micromodel representative of a second hydrocarbon-carrying formation different from the first hydrocarbon-carrying formation, flow through the second fluidic flow pathway representative of flow through the second hydrocarbon-carrying formation; and
a fluid inlet formed on the substrate, the fluid inlet fluidically configured to simultaneously flow fluid to the first fluidic flow pathway and the second fluidic flow pathway.

2. The apparatus of claim 1, wherein the first hydrocarbon-carrying formation is an ideal hydrocarbon-carrying formation, the first porous micromodel comprises first porous media defining a first plurality of pores that defines the first fluidic flow pathway, the first plurality of pores having substantially identical dimensions.

3. The apparatus of claim 2, wherein the first plurality of pores are substantially equidistantly spaced apart from each other.

4. The apparatus of claim 3, wherein each of the first plurality of pores is circular, wherein the first plurality of pores has substantially the same diameter.

5. The apparatus of claim 1, wherein the second hydrocarbon-carrying formation is an actual hydrocarbon-carrying formation, the second porous micromodel comprises second porous media defining a second plurality of pores that defines the second fluidic flow pathway, the second plurality of pores having a range of varying dimensions.

6. The apparatus of claim 5, wherein the second plurality of pores are spaced at varying distances from each other.

7. The apparatus of claim 1, further comprising:
a first porous micromodel fluid inlet formed on the substrate at an edge of the first porous micromodel, the first porous micromodel fluid inlet fluidically connected to the fluid inlet formed on the substrate, the first porous micromodel fluid inlet configured to receive fluid from the fluid inlet and to flow the fluid into the first fluidic pathway; and
a second porous micromodel fluid inlet formed on the substrate at an edge of the second porous micromodel, the second porous micromodel fluid inlet fluidically connected to the fluid inlet formed on the substrate, the second porous micromodel fluid inlet configured to receive fluid from the fluid inlet and to flow the fluid into the second fluidic pathway.

8. The apparatus of claim 7, wherein the first porous micromodel fluid inlet and the second porous micromodel fluid inlet have the same dimensions.

9. The apparatus of claim 7, further comprising:
a first porous micromodel fluid outlet formed on the substrate at another edge of the first porous micromodel, the first porous micromodel fluid outlet configured to permit the fluid flowed through the first fluidic pathway to exit the first porous micromodel; and
a second porous micromodel fluid outlet formed on the substrate at another edge of the second porous micromodel, the second porous micromodel fluid outlet configured to permit the fluid flowed through the second fluidic pathway to exit the second porous micromodel.

10. The apparatus of claim 1, wherein the substrate is made of silicon wafer, wherein the apparatus further comprises a transparent plate that fluidically seals the first porous micromodel and the second porous micromodel.

11. The apparatus of claim 1, further comprising a wall between the first porous micromodel and the second porous micromodel, the wall fluidically isolating the first porous micromodel from the second porous micromodel.

12. A laboratory-scale system comprising:
a porous micromodel network comprising a plurality of porous micromodels that are different from each other and that are fluidically isolated from each other, each porous micromodel defining a respective fluidic flow pathway, each porous micromodel representative of a respective hydrocarbon-carrying formation, flow through the each fluidic flow pathway representative of flow through the respective hydrocarbon-carrying formation; and
a fluid flow device configured to simultaneously flow fluid through the porous micromodel network.

13. The system of claim 12, further comprising a flow manifold comprising an inlet fluidically coupled to the fluid flow device and a plurality of outlets, one outlet per porous micromodel, the plurality of outlets fluidically coupled to a respective plurality of porous micromodel inlets, the flow manifold configured to receive fluid from the fluid flow device and simultaneously flow the fluid to the porous micromodel network.

14. The system of claim 12, further comprising a plurality of pressure gauges, one pressure gauge per porous micromodel, the plurality of pressure gauges coupled to the respective plurality of porous micromodels, each pressure gauge configured to measure a flow pressure of the fluid through the respective porous micromodel.

15. The system of claim 12, further comprising a flow visualization device spatially positioned relative to the porous micromodel network, the flow visualization device configured to capture flow and saturation of the fluid through each porous micromodel.

16. The system of claim 15, wherein the flow visualization device comprises a camera.

17. The system of claim 16, wherein the flow visualization device comprises a microscope coupled to the camera.

18. The system of claim 12, wherein the fluid flow device comprises a pump configured to pump the fluid through the porous micromodel network.

19. The system of claim 18, further comprising a plurality of fluid containers, each fluid container carrying a hydrocarbon-carrying formation fluid, the pump configured to draw the hydrocarbon-carrying formation fluid from one of the plurality of fluid containers and flow the hydrocarbon-carrying formation fluid simultaneously through the porous micromodel network.

20. A method comprising:
simultaneously flowing a plurality of fluids through a respective, plurality of laboratory-scale porous micromodels of a porous micromodel network, the plurality of porous micromodels fluidically isolated from each other, each porous micromodel defining a respective fluidic flow pathway, each porous micromodel representative of a respective hydrocarbon-carrying formation, flow through the each fluidic flow pathway representative of flow through the respective hydrocarbon-carrying formation;
imaging flow of the plurality of fluids through the respective, plurality of porous micromodels; and
evaluating flow through each respective hydrocarbon-carrying formation based on imaging the flow and the saturation of the fluid.

21. The method of claim 20, wherein the plurality of laboratory-scale micromodels comprises two porous micromodels and the plurality of fluids comprises two same fluids.

22. The method of claim 20, wherein the plurality of laboratory-scale micromodels are different from each other.

* * * * *